United States Patent
Lee et al.

(10) Patent No.: US 8,504,166 B2
(45) Date of Patent: Aug. 6, 2013

(54) DEEP BRAIN STIMULATION DEVICE HAVING WIRELESS POWER TRANSMISSION MECHANISM

(75) Inventors: Uhn Lee, Incheon (KR); Sang Hyouk Choi, Poquoson, VA (US)

(73) Assignee: Gachon University of Medicine & Science Industry-Academic Cooperation Foundation, Incheon (KR)

( * ) Notice: Subject to any disclaimer, the term of this patent is extended or adjusted under 35 U.S.C. 154(b) by 390 days.

(21) Appl. No.: 12/600,026

(22) PCT Filed: May 14, 2008

(86) PCT No.: PCT/KR2008/002663
§ 371 (c)(1),
(2), (4) Date: Jun. 22, 2010

(87) PCT Pub. No.: WO2008/140242
PCT Pub. Date: Nov. 20, 2008

(65) Prior Publication Data
US 2011/0112602 A1 May 12, 2011

(30) Foreign Application Priority Data
May 14, 2007 (KR) ........................ 10-2007-0046404

(51) Int. Cl.
*A61N 1/08* (2006.01)
(52) U.S. Cl.
USPC .......................................................... 607/61
(58) Field of Classification Search
USPC ................... 607/45, 46, 48, 49, 61
See application file for complete search history.

(56) References Cited

U.S. PATENT DOCUMENTS

| | | | |
|---|---|---|---|
| 6,427,086 | B1 | 7/2002 | Fischell et al. |
| 7,013,177 | B1 | 3/2006 | Whitehurst et al. |
| 2005/0187488 | A1 | 8/2005 | Wolf |
| 2005/0283202 | A1 | 12/2005 | Gellman |
| 2006/0149338 | A1* | 7/2006 | Flaherty et al. .................. 607/49 |
| 2006/0184209 | A1 | 8/2006 | John et al. |
| 2006/0212097 | A1 | 9/2006 | Varadan et al. |

FOREIGN PATENT DOCUMENTS

KR 10-2007-0005982 A 1/2007

OTHER PUBLICATIONS

International Search Report of International Application No. PCT/KR2008/002663, filed May 14, 2008, International Publication No. WO 2008/140242 A1, published Nov. 20, 2008, of Gachon University of Medicine # Science Industry-Academic Cooperation Foundation, of inventors Uhn Lee et al., for a Deep Brain Stimulation Device Having Wireless Power Transmission Mechanism.

\* cited by examiner

*Primary Examiner* — Tammie K Heller
(74) *Attorney, Agent, or Firm* — Patent Office of Dr. Chung Park

(57) ABSTRACT

Provided is a deep brain stimulation (DBS) device that wirelessly receives microwaves from a power transmission antenna installed at a hat put on a patient, transforms the microwaves into power, and drives electrodes implanted into a brain of the patient using the power, so as to correct abnormal motor and sensory functions of the patient. The DBS device includes: a hat module configured for placement over a head of the patient to transmit microwaves, and an implantation module configured to be implanted through a skull under a scalp to contact the cerebral nerve of the patient, receive the microwaves from the hat module, transform the microwaves into direct current (DC) power, and stimulate the cerebral nerve using the DC power.

9 Claims, 3 Drawing Sheets

DEEP BRAIN STIMULATION DEVICE HAVING WIRELESS POWER TRANSMISSION MECHANISM

CROSS REFERENCES TO RELATED APPLICATIONS

This application is a national phase application based upon priority International PCT Patent Application No. PCT/KR2008/002663 filed 14 May 2008, International Publication No. WO/2008/140242 A1 published 20 Nov. 2008, which is based upon priority Korean Patent Application No. 10-2007-0046404 filed 14 May 2007.

BACKGROUND OF THE INVENTION

1. Technical Field

The present invention relates to a deep brain stimulation (DBS) device using a wireless power transmission mechanism, and more particularly, to a DBS device which wirelessly receives microwaves from a power transmission antenna installed at a hat put on a patient, transforms the microwaves into power, and drives electrodes implanted into a brain of the patient using the power, so as to correct abnormal motor and sensory functions using power which is wirelessly transmitted from an outside into the patient.

2. Background Art

Modern people are exposed to accidents or diseases and thus lose their own functions or motors due to complexity of a modern society. There are limits to cures for such patients only through medical science. Medical and biological engineering in which an engineering field is grafted into a medical field has been developed in order to overcome the above-described limits. Thus, many areas of a health management system have been changed.

For example, cardiac pacemakers and defibrillators have saved lives of hundreds of people and cured heart diseases. Also, surgeons implant deep brain stimulation (DBS) devices into brains of patients to control abnormal brain functions of the patients using techniques of cardiac pacemakers.

Abnormal physical actions or mental disorders derive from abnormal functions of brains such as Parkinson's disease or an obsessive-compulsive disorder (OCD). Parkinson's disease is a chronic degenerative disease whose main symptoms are shivering of hands and feet, slow actions, and hardening of muscles.

Neurosurgeons use DBS devices to cure health problems such as Parkinson's disease, OCD, and hypochondria. A curing method using a DBS device is a surgical method for curing an OCD and is effective in curing Parkinson's disease. This curing method requires a process of implanting an electrode, which inhibits or stimulates a predetermined part of a cerebral nerve, into a deep part of a brain in order to normalize a function of the brain of a patient.

Operations using DBS devices have been performed since Alim-Louis Benabid in the Grenoble University Hospital of France reported on 80 or more Parkinson's disease patients in 1993. Thus, about thirty thousand similar operations have been very successfully performed throughout the world. Such a DBS device applies current pulses to a cerebral nerve through electrodes, which are implanted into an accurate position of the cerebral nerve, in order to stop shivering, which is a main symptom of a disease, and relax stooped muscles. DBS devices contribute to controls of extant diseases. However, when a DBS device uses an electric wire in a human body to supply power, transmit data, and program software, a plurality of problems occur.

FIG. 1 illustrates a conventional DBS device which is implanted into a human body. Referring to FIG. 1, the conventional DBS device includes an electrode needle 146 and a power supply unit 160. The electrode needle 146 is implanted into a cerebral nerve to provide an electric stimulation to the cerebral nerve so as to restore an abnormal function of a brain. The power supply unit 160 is connected to the electrode needle 146 through an electric wire 150 to supply power to the electrode needle 146.

The conventional DBS device having the above-described structure sews the power supply unit 160 having a power source such as a battery into abdomen or thorax to be turned on or off by remote control using a skin. Thus, the DBS device is clinically simply used. However, the DBS device provides hard inconvenience to a patient. Also, if the electric wire 550 installed underneath the skin of the patient short-circuits or power of the battery installed in the abdomen or thorax is consumed, a surgical operation is repeatedly performed to replace or repair a corresponding part.

BRIEF SUMMARY OF THE INVENTION

Disclosure of Invention Technical Problem

The present invention provides a deep brain stimulation (DBS) device which electrically stimulates a cerebral nerve of a patient using power which is transmitted as microwaves from an outside into a body of the patient, instead of implanting an additional power supply device supplying power by wire, in order to exclude an additional surgical operation for replacing and repairing a power system.

Advantageous Effects

A deep brain stimulation (DBS) device using a wireless power transmission mechanism according to the present invention may wirelessly receive power to normalize an abnormal cerebral nervous system of a patient and strengthen weakened functions of the cerebral nervous system. Also, the DBS device may not include an additional power supply device which is implanted into a human body and thus does not require an additional operation for replacing a power source and an electric wire. Thus, maintenance cost of the DBS device may be considerably saved, and pains of a patient caused by repeated operations may be relieved.

A more detailed explanation of the invention is provided in the following detailed description and appended claims taken in conjunction with the accompanying drawings.

BRIEF DESCRIPTION OF THE DRAWINGS

FIG. 1 illustrates a conventional deep brain stimulation (DBS) device which is implanted into a human body.

FIG. 2 illustrates a DBS device using a wireless power transmission mechanism according to an embodiment of the present invention.

DETAILED DESCRIPTION OF THE INVENTION

Figure 3:
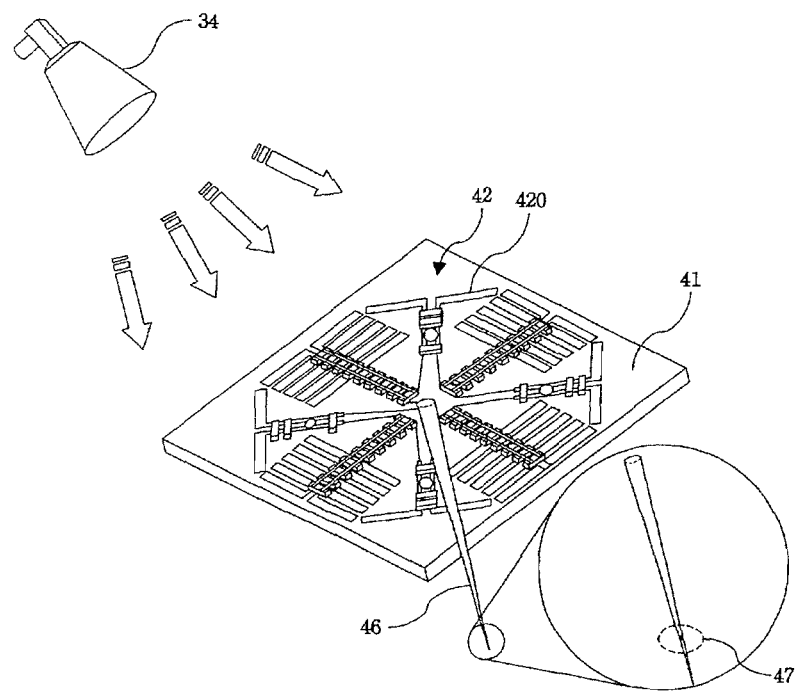
FIG. 3 is a perspective view of parts of a wireless power transmission module of FIG. 2.

The following is a detailed description and explanation of the preferred embodiments of the invention and best mode for practicing the invention.

BEST MODE FOR CARRYING OUT THE INVENTION

According to an aspect of the present invention, there is provided a deep brain stimulation (DBS) device using a wireless power transmission mechanism, including: a hat module which is installed at a hat put on a head of the patient to transmit microwaves; and an implantation module which is implanted through a skull under a scalp to contact the cerebral nerve of the patient, receives the microwaves from the hat module, transforms the microwaves into direct current (DC) power, and stimulates the cerebral nerve using the DC power.

MODE FOR THE INVENTION

Exemplary embodiments of the present invention will now be described in detail with reference to the attached drawings.

Figures 1, 2:
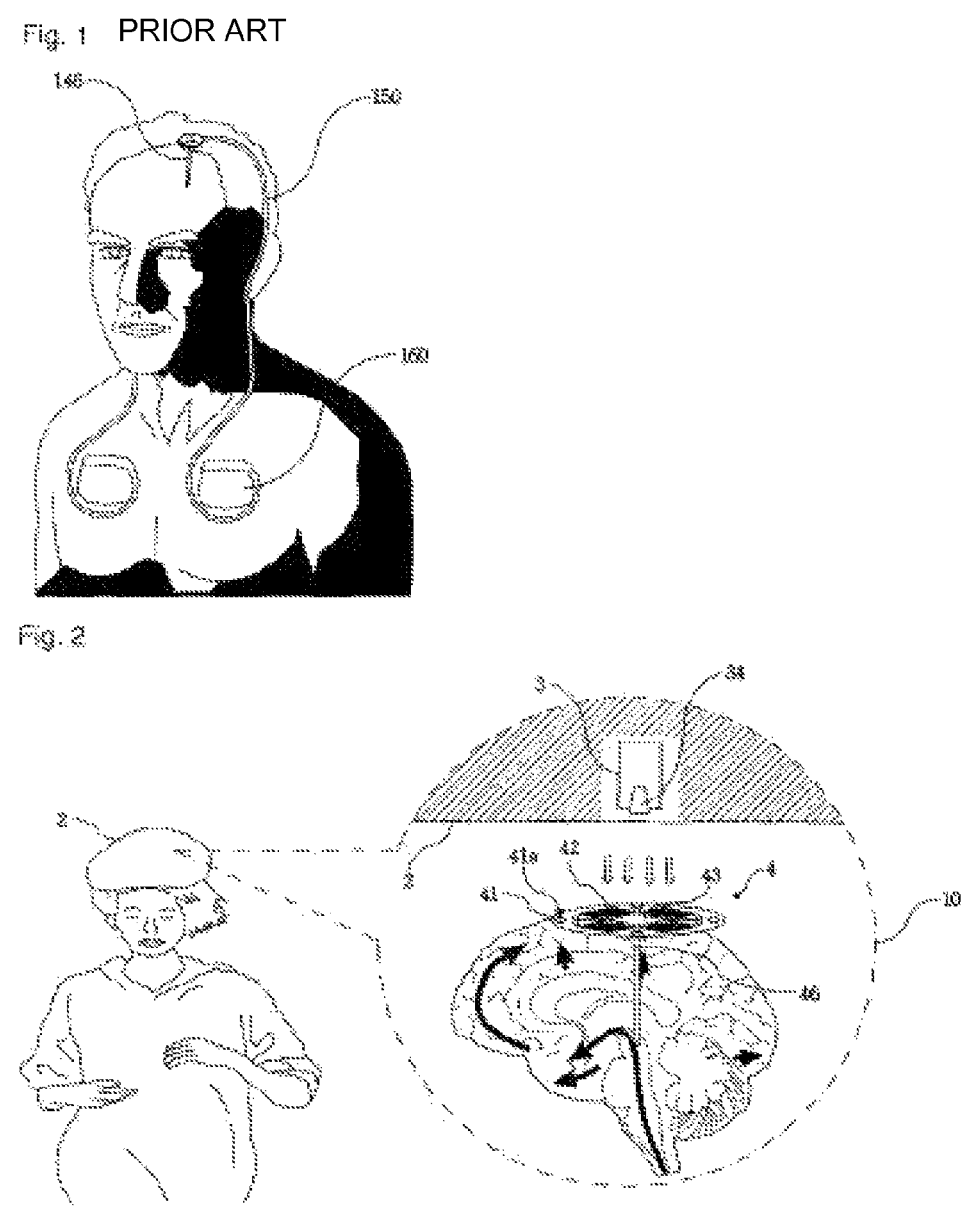

FIG. 2 illustrates a DBS device using a wireless power transmission mechanism according to an embodiment of the present invention. Referring to FIG. 2, a DBS device 10 according to the present embodiment includes an implantation module 4 and a hat module. The implantation module 4 is implanted into a head of a patient.

The hat module 3 is installed inside a hat 2, which is put on the head of the patient, to wirelessly transmit power required by the implantation module 4. The hat module 3 includes a power transmission antenna 34, which transmits microwaves, to wirelessly transmit power, which required for driving the implantation module 4, to the implantation module 4. Here, the hat module 3 may include a controller 31 and a command signal transmitter 35 shown in FIG. 6. The controller 31 controls the whole module functions including a power transmission function of the power transmission antenna 34. The command signal transmitter 35 transmits a command signal to operate a cerebral nerve stimulation function, to the implantation module 4.

The implantation module 4 includes a stimulation pin 46, a thin film 41, and a power receiver 42. The stimulation pin 46 is implanted through a skull under a scalp to contact a deep cerebral nerve so as to provide an electric stimulation to a cerebral nerve of the patient. The thin film 41 is installed at the skull under the scalp. The power receiver 42 is installed on the thin film 4 to receive power for driving the stimulation pin 46 from the hat module 3. The implantation module 4 further includes a power and signal processor 43 which is connected to the power receiver 42 to modulate direct current output from the power receiver 42 and process a command signal received from the hat module 3.

Here, the thin film 41 is formed of a flexible material and includes a plurality of screw holes 41a which are formed in a main part of the thin film 4 and screwed to the scalp through screws. The stimulation pin 46 is connected to a center of a lower surface of the thin film 41 to be fixed to a position in which a nerve stimulation is to be provided.

The power transmission antenna 34 of the hat module 3 and the transmission receiver 42 of the implantation module 4 constitute a wireless power transmission module to wirelessly transmit power so as to supply power for driving the stimulation pin 46 without installing an additional power source into a body of the patient.

FIG. 3 is a perspective view of parts of the wireless power transmission module of FIG. 1 to illustrate a wireless power transmission performed between the implantation module 4 and the hat module 3.

A wireless power transmission according to the present invention uses an electric wave transmission method of transforming power energy into microwaves advantageous to a wireless transmission and transmitting the microwaves. In other words, the microwaves are transmitted from the power transmission antenna 34 of the hat module 3 to the power receiver 42 of the implantation module 4, and the power receiver 42 of the thin film 41 transforms the microwaves into necessary power.

As shown in FIG. 3, the power transmission antenna 34 is a microwave antenna which transmits the microwaves to the transmission receiver 42 of the implantation module 4. The power transmission antenna 34 may be a horn antenna including a waveguide whose end part is trumpet-shaped so as to directly transmit the microwaves to space. Here, the transmitted microwaves may have power within 2 watt and frequency lower than an X-band (10 GHz) so as to reduce a size of the transmission receiver 42 and easily pass through an air gap and the scalp between the power transmission antenna 34 and the transmission receiver 42. However, power may be attenuated in a frequency of 3 GHz or less due to a hydroxyl group (OH) and resonant coupling of a skin tissue. Thus, the frequency of the microwaves may be set to a range between 3 GHz and 10 GHz.

The transmission receiver 42, which receives the microwaves transmitted from the power transmission antenna 34, is a rectenna array which includes a plurality of rectennas 420 which are installed on an upper surface of the thin film 41 positioned between the scalp and the skull. The transmission receiver 42 transforms the microwaves into direct current (DC) power. Here, the transmission receiver 42, i.e., the rectenna array, may be radially disposed on the upper surface of the thin film 41 to obtain maximum coupling and average power regardless of polarization of the microwaves. Structure and detailed operations of the rectennas 420 constituting the transmission receiver 42 will be described in detail later.

The DC current generated by the transmission receiver 42 is modulated into pulse current for stimulating the cerebral nerve through the power and signal processor 43 shown in FIG. 2 and then supplied to the stimulation pin 46 connected to the center of the lower surface of the thin film 41.

The stimulation pin 46 is implanted into a micro-path of an activity cerebral cortex so that a lower part of the stimulation pin 46 contacts the cerebral nerve. A body of the stimulation pin 46 may be formed of a material which does not react to and reject fluid in a human body. In particular, the body of the stimulation pin 46 may be formed of a polymer or ceramic material which is physiologically well adapted to the human body.

A plurality of stimulation electrodes 47 are installed at a lower end of the stimulation pin 46 to transmit a voltage 8 for stimulating a nervous cell. An insulating material is coated on surfaces of the stimulation electrodes 47 and a tip area to prevent an electric leakage to the body of the patient. Here, the plurality of stimulation electrodes 47 installed inside the stimulation pin 46 are formed of insulation coated gold lines.

The stimulation pin 46 is an only part which is implanted into a brain for DBS. The power receiver 42 of the thin film 41 positioned between the scalp and the skull is combined with the microwaves which are transmitted from the hat module 3 to generate power necessary for performing a function of the stimulation pin 46. Power is wirelessly transmitted using the power transmission antenna 34 and the power receiver 42 which are opposite to each other so that the air gap is positioned between the power transmission antenna 34 and the power receiver 42, so as to stably supply power used by the implantation module 4.

Figure 4:
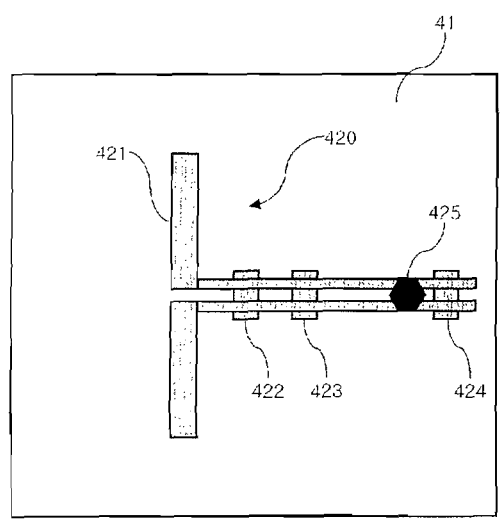
FIG. 4 illustrates a structure of a rectenna of FIG. 3.
Figure 5:
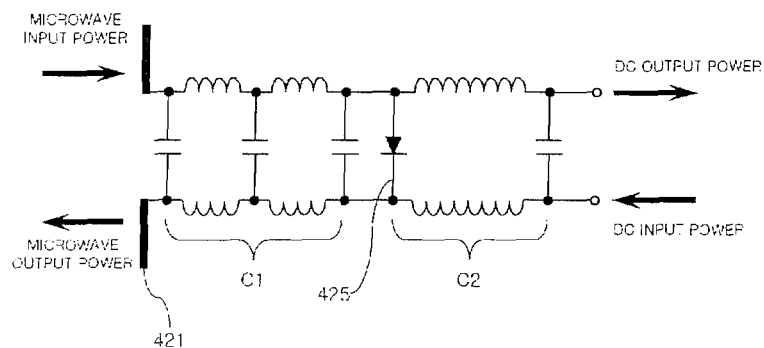
FIG. 5 is an equivalent circuit diagram of the rectenna of FIG. 4.

FIG. 4 illustrates a structure of the rectenna 420 of FIG. 3, and FIG. 5 is an equivalent circuit diagram of the rectenna 420 of FIG. 4.

As shown in FIG. 4, the rectenna 420 has a structure in which a half-wave dipole antenna 421, a plurality of condensers 422, 423, and 424, and a schottky diode 425 are connected to each other. Here, the condensers 422, 423, and 424 operate as filters, and the schottky diode 425 operates as a rectifier using a schottky barrier. The rectenna 420 receives microwave power propagated through the space and transforms the microwave power into a DC. The rectenna 420 is transposed into an equivalent circuit, and an operation of the equivalent circuit will now be described.

As shown in FIG. 5, if the rectenna 420 operates in a normal mode, the microwave power is input through the half-wave dipole antenna 421, transformed into the DC power through a rectifier circuit C2 including the schottky diode 425, and output to load. If the rectenna 420 operates in a reverse mode, the input DC power is transformed into microwaves through the rectifier circuit C2 and propagated to the space through the half-wave dipole antenna 421. Here, a low-pass filter C1 is installed between the half-wave dipole antenna 421 and the rectifier circuit C2 to prevent a high frequency generated during a rectifying process from being re-radiated through the half-wave dipole antenna 421 and interrupting communications.

The rectenna 420 having the above-described structure determines a coupled frequency band according to lengths and the number of half-wave dipole antennas 421. Thus, rectennas including dipole antennas having appropriate lengths and the appropriate number may be constituted in consideration of a frequency band of microwaves to form the rectenna array of the transmission receiver 42 so as to maximize coupling to the microwaves transmitted from the power transmission antenna 34.

Figure 6:
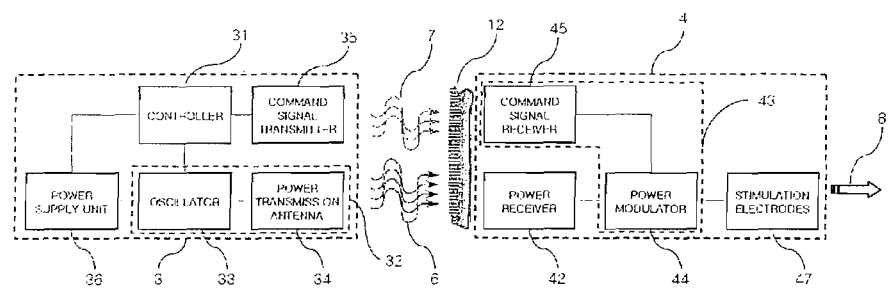
FIG. 6 is a block diagram of a DBS device using a wireless power transmission mechanism according to an embodiment of the present invention.

FIG. 6 is a block diagram of the DBS device using the wireless power transmission mechanism.

A whole structure and an operation of the DBS device 10 will now be described in detail with reference to FIG. 6.

As previously described, the DBS device 10 includes the hat module 3 which is installed inside the hat 2 put on the patient and the implantation module 4 which is implanted into the brain of the patient.

The hat module 3 includes a power supply unit 36, the power transmitter 32, a command signal transmitter 35, and a controller. The power supply unit 36 supplies power to the hat module 3, and the power transmitter 32 transmits the microwave power. The command signal transmitter 35 transmits a command signal to operate the cerebral nerve stimulation function of the implantation module 4. The controller 31 controls a microwave transmission function of the power transmitter 32 or transmits a cerebral nerve stimulation command signal 7 to the implantation module 4 through the command signal transmitter 35. The transmitter 32 includes an oscillator 33 which receives power from the power supply unit 36 to generate microwaves to be transmitted and the power transmission antenna 34 which transmits the microwaves 6 generated by the oscillator 33 to the implantation module 4.

The implantation module 4 implanted into the brain includes the stimulation pin 46, the power receiver 42, a power modulator 44, and a command signal receiver 45. The stimulation pin 46 includes the stimulation electrodes 47. The power receiver 42 receives the microwave power, which is transmitted from the power transmission antenna 34 of the hat module 3 through a scalp 12, and transforms the microwave power into the DC power. The power modulator 44 receives the DC power from the power receiver 42 and modulates the DC power into power which is to be used by the whole circuit, the stimulation pin 46, etc. The command signal receiver 45 receives a command signal from the command signal transmitter 35 of the hat module 3.

As described above, the power receiver 42 may be constituted as the rectenna array which is radially disposed on the thin film 41 fixed between the scalp and the skull. In this case, the receiver 42 receives the microwave power through the half-wave dipole antennas 421 of the rectennas 420 and the schottky diodes 425 connected to the halfwave dipole antennas 421 and transforms the microwave power into DC power.

The power output from the power modulator 44 may be the pulse wave which has the frequency of 200 Hz or less, the pulse width between 60 μsec and 500 μsec, and the magnitude between 0V and ±10V in order to stimulate a deep brain.

As described above, in the wireless power transmission of the present embodiment, the microwave power generated by the oscillator 33 of the hat module 3 is transmitted to the power receiver 42 of the implantation module 4 through the power transmission antenna 34. Next, the microwave power is transformed into the DC power and then modulated into a DC current having a predetermined voltage necessary for driving a system and a pulse current for stimulating the cerebral nerve by the power modulator 44. The DC current and the pulse current are supplied to the whole circuit and the stimulation electrodes 47 of the hat module 4.

In other words, power necessary for driving the implantation module 4 is not directly transmitted but is generated by the rectenna array which is combined with the microwave which is transmitted from the hat module 3 through a thickness of a skin tissue.

The hat module 3 further includes a switch (not shown) which is connected to the controller 31 and turns on and/or off the cerebral nerve stimulation function of the implantation module 4. Thus, the controller 31 drives the oscillator 33 according to an operation of the switch and transmits a nerve stimulation command signal to the command signal receiver 45 of the implantation module 4 through the command signal transmitter 35. Also, the power modulator 44 operates according to the nerve stimulation command signal received through the command signal receiver 45 to supply the pulse power to the stimulation electrodes 47 so as to stimulate the cerebral nerve.

Here, the command signal transmitter 35 and the command signal receiver 45 may not be installed, and the power receiver 42 may receive the microwave power from the power transmission antenna 34 and transform the microwave into the DC power according to driving of the oscillator 33. Also, the power modulator 44 may immediately operate to supply the pulse power to the stimulation electrodes 47.

A patient, who is implanted with the DBS device 10 having the above-described structure, is able to freely move with the hat 2 adjacent to the thin film 41 implanted into a head of the patient. If an abnormal symptom, such as hand shivering of a patient with a Parkinson's disease, occurs in a cerebral nerve of the patient, the patient or another person immediately operates the switch installed at the hat 2 to transmit power of the hat module 3 in a microwave form to the power receiver 42 positioned under the scalp, i.e., the rectenna array. Next, the DBS device 10 generates pulse power from the microwave power to operate the stimulation pin 46 so as to solve the abnormal symptom of a brain of the patient.

As described above, a DBS device using a wireless power transmission mechanism according to the present invention is sewed into abdomen or thorax to be turned on and/or off by remote controls through a skin. Compared to a conventional DBS device, the DBS device of the present invention wirelessly transmits power. Thus, the DBS device does not require a surgical operation which is performed to replace a battery and other elements implanted into a body of a patient.

While the present invention has been particularly shown and described with reference to exemplary embodiments thereof, it will be understood by those of ordinary skill in the art that various changes in form and details may be made therein without departing from the spirit and scope of the present invention as defined by the following claims.

INDUSTRIAL APPLICABILITY

A DBS device using a wireless power transmission mechanism according to the present invention normalizes functions of a patient with an abnormal cerebral nervous system and strengthens weakened functions of the cerebral nervous system. Also, the DBS device permanently operates through only a one-time operation.

Although embodiments of the invention have been shown and described, it is to be understood that various modifications, substitutions, and rearrangements of parts, components, and/or process (method) steps, as well as other uses of the DBS device, can be made by those skilled in the art without departing from the novel spirit and scope of this invention.

What is claimed is:

1. A deep brain stimulation (DBS) device using a wireless power transmission mechanism to stimulate a cerebral nerve of a patient having abnormal motor and sensory functions so as to normalize functions of a brain of the patient, the DBS device comprising:
    a hat module configured for placement over a head of the patient and further configured to transmit microwaves; and
    an implantation module, including:
        a thin film configured to be fixed between a scalp and a skull of the patient;
        a power receiver disposed on the thin film and configured to receive the microwaves from the hat module through the scalp and transform the microwaves into DC power;
        a power modulator disposed on the thin film and configured to receive the DC power from the power receiver and modulate the DC power into power to be used by the implantation module; and
        a stimulation pin having a head portion that is directly attached to a lower surface of the thin film, the stimulation pin being configured to be implanted through the skull under the scalp of the patient to thereby contact a deep cerebral nerve and further configured to provide an electric stimulation to the cerebral nerve of the patient.

2. The DBS device of claim 1, wherein:
    the hat module comprises a power transmission antenna configured to transmit the microwaves to the implantation module; and
    the power receiver is configured to receive the microwaves from the power transmission antenna.

3. The DBS device of claim 2, wherein the power transmission antenna is a horn antenna.

4. The DBS device of claim 1, wherein the hat module comprises:
    a power supply unit configured to supply power to the hat module;
    a power transmitter configured to transmit the microwaves;
    a command signal transmitter configured to transmit a command signal to operate a cerebral nerve function of the implantation module; and
    a controller configured to control the power transmitter and the command signal transmitter.

5. The DBS device of claim 4, wherein the power transmitter comprises:
    an oscillator configured to receive power from the power supply unit to generate the microwaves; and
    a power transmission antenna configured to transmit the microwaves to the implantation module.

6. The DBS device of claim 4, wherein the implantation module comprises:
    a command signal receiver disposed on the thin film and configured to receive the command signal from the command signal transmitter of the hat module.

7. The DBS device of claim 5, wherein the power transmission antenna is a horn antenna.

8. The DBS device of claim 1, wherein the power receiver is a rectenna array which is radially disposed on the thin film.

9. The DBS device of claim 1, wherein the stimulation pin includes at least one stimulation electrode installed at a tip portion thereof and insulation material coated on a surface thereof.

* * * * *